United States Patent [19]

Cole

[11] Patent Number: 4,532,330

[45] Date of Patent: Jul. 30, 1985

[54] PROCESS FOR PRODUCING DENSIFIED HALOGENATED DIMETHYLHYDANTOINS

[75] Inventor: Leon M. Cole, West Lafayette, Ind.

[73] Assignee: Great Lakes Chemical Corporation, West Lafayette, Ind.

[21] Appl. No.: 429,160

[22] Filed: Sep. 30, 1982

[51] Int. Cl.³ .................. C07D 211/72; C07D 211/84
[52] U.S. Cl. .................................................... 548/311
[58] Field of Search ............................... 548/308, 311

[56] References Cited

U.S. PATENT DOCUMENTS

| | | | |
|---|---|---|---|
| 2,130,805 | 9/1938 | Levine | 548/311 |
| 2,392,505 | 1/1946 | Rogers | 548/311 |
| 2,398,598 | 4/1946 | Rogers | 548/311 |
| 2,779,764 | 1/1957 | Paterson | 548/311 |
| 2,795,556 | 6/1957 | Quinn | 548/311 |
| 2,868,787 | 1/1959 | Paterson | 548/311 |
| 2,920,997 | 1/1960 | Wolf et al. | 548/311 |
| 3,121,715 | 2/1964 | Waugh et al. | 548/311 |
| 3,345,371 | 8/1965 | Paterson | 548/311 |

Primary Examiner—John Kight
Assistant Examiner—Kriellion Morgan
Attorney, Agent, or Firm—Kirkland & Ellis

[57] ABSTRACT

Halogenated dimethylhydantoins are intimately mixed wth calcium chloride and water and compressed to provide a densified particulate solid that is capable of withstanding the stresses of automatic packaging, conveying and handling.

11 Claims, No Drawings

PROCESS FOR PRODUCING DENSIFIED HALOGENATED DIMETHYLHYDANTOINS

BACKGROUND OF THE INVENTION

A. Field of the Invention

The present invention discloses a novel method for the synthesis of dihalogenated dimethylhydantoins intimately mixed with calcium chloride and water to form densified particulate solids that withstand the stresses of automatic packaging, conveying, and handling.

B. Description of the Prior Art

Halogenated dimethylhydantoins containing bromine and/or chlorine have the following structure:

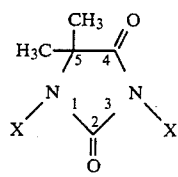

where X is bromine or chlorine. Such halogenated dimethylhydantoins are useful as bacteriocides in water treatment processes because they provide a source of active halogen in low concentrations. They are also highly efficient donors for effecting various organic syntheses.

The use of additives in agglomeration of compounds is well known in the literature, with the number of additives used being as large as the number of compounds compacted or agglomerated. Calcium chloride has been used as a curing agent in the cement industry, and the use of water as an adhesive in agglomeration is also known. However, calcium chloride and water in intimate mixture with halogenated compounds has not heretofore been employed.

Halogenated dimethylhydantoins are produced as particulate solids, and for certain uses it is desired to compact, agglomerate, extrude, or otherwise densify these particulate solids into tablets or other geometrical shapes with sufficient strength to withstand automatic packaging, conveying, and handling. When densified without additives, these compounds lack the strength to withstand such operations. Moreover, many compounds commonly used in the densification industry to give strength to agglomerates will chemically react or otherwise interfere with the desired uses of halogenated hydantoins.

U.S. Pat. No. 3,412,021 discloses the use of a variety of binders, principally polyvalent metal hydroxides, in preparing solid forms of N-halogenated organic compounds. This patent, however, does not teach the use of calcium chloride and water as densification or agglomeration agents in the preparation of solid halogenated dimethylhydantoins and thus does not render Applicant's methods or compositions unpatentable.

It is a primary object of this invention to obtain a method of producing halogenated dimethylhydantoins having superior strength.

It is another object of this invention to create densified halogenated dimethylhydantoins which withstand automated packaging and handling, without interfering with other desired uses of the subject compounds.

SUMMARY OF THE INVENTION

The foregoing and other objects, advantages, and features may be obtained by intimately mixing halogenated hydantoins with calcium chloride and water. More particularly, calcium chloride and water when mixed with halogenated dimethylhydantoins give densified shapes with sufficient strength to endure automated operations without reacting or otherwise interfering with the desired uses of these products.

Preferably, the halogenated dimethyl hydantoin is produced with calcium chloride formed in situ by the method of halogenating dimethyl hydantoin with a first halogenation agent in the presence of water and source of calcium and hydroxide ions in order to form a monohalogenated intermediate. Thereafter, the monohalogenated intermediate is halogenated with a second halogenation agent in the presence of water and a source of calcium and hydroxide ions, at least one of the first and second halogenation agents including a source of chlorine. The dihalogenated hydantoin thereby formed is separated from the reaction mixture without washing, and after densification contain calcium chloride and water, preferably at the level of about 2 to 6% and 1 to 5% respectively.

DESCRIPTION OF THE PREFERRED EMBODIMENTS

In accordance with the present invention, it has been discovered that when the calcium chloride and water are mixed with the halogenated (i.e., bromine and/or chlorine-containing) dimethylhydantoins, the material can be compacted, agglomerated, extruded, or otherwise densified into shapes with sufficient strength to withstand mechanical and automated packaging and handling operations. Preferably, calcium chloride is provided in intimate mixture by its concurrent production in situ with the halogenated dimethylhydantoins. It is believed that the superior crush strength of the densified solid is due to the intimately mixed nature of the solids and water.

The process of this invention is employed in the preparation of densified dihalogenated dimethylhydantoins, especially bromochlorodimethylhydantoin, dibromodimethylhydantoin, and dichlorodimethylhydantoin. These materials are prepared by the reaction of dimethylhydantoin, and the corresponding source of halogen in water. The halogenation step is carried out in the presence of base to neutralize the acid formed in the halogenation step. Although almost any inorganic source of —OH will do, sodium hydroxide, potassium hydroxide, and calcium hydroxide can be used. The inorganic source of —OH and the halogenating agent are added concurrently at such a rate that the pH is maintained in the range of about 6.8–7.0 and the temperature is maintained at about 25° centigrade.

When the base used in the halogenation steps is sodium hydroxide or potassium hydroxide, at the end of the halogenation step, the product is typically washed and dried leaving the dihalogenated dimethylhydantoin as a dry solid. In order to prepare the particulate solid in a form suitable for densification, calcium chloride and water are added to the dried dihalogenated dimethylhydantoin and mechanically mixed with the solid. The product dihalogenated dimethylhydantoin intimately mixed with calcium chloride and water is now suitable for extrusion or for compression into a desired shape.

Preferably the calcium chloride is prepared concurrently with the dihalogenated dimethylhydantoins by employing calcium hydroxide as the base. After the halogenation step, if the dihalogenated dimethylhydantoin is filtered and not washed, the bi-product calcium chloride contained in the mother liquor is retained intimately mixed in the product. After the majority of the mother liquor is removed by filtration of the product, the wet solids may be then densified into the desired shapes or extruded.

The amount of calcium chloride and water is desirably controlled so that the densified product consists of about 1-5% water by weight and about 2-6% calcium chloride by weight.

When the halogenated dimethylhydantoins are prepared, washed and dried and then calcium chloride and water is added and mechanically mixed with the solids, the densified solids prepared therefrom have exhibited higher crush strengths than the densification product formed from the pure halogenated dimethylhydantoin. The extent to which the halogenated dimethylhydantoins possess greater crush strengths when mechanically mixed with calcium chloride and water depends on the efficiency and the length of the mechanical mixing.

Generally, stoichiometric or slight excess amounts of the halogenation agents are employed, with the amount of base being that required to achieve a very slightly acidic pH.

In the preferred process water and dimethylhydantoin are added to the reactor, the water being in a four to five fold ratio by weight. Bromine (one-half mole per mole of dimethylhydantoin) and an aqueous slurry of calcium hydroxide (one-fourth mole per mole of dimethylhydantoin) are added simultaneously at a rate that the temperature is controlled at about 25° C. and the pH is controlled at about 6.8-7.0. After the bromine addition is completed, chlorine (one and one-half moles per mole of dimethylhydantoin) and calcium hydroxide (three-fourths mole per mole of dimethylhydantoin) were added at a rate to again control the pH at about 6.8-7.0 and the temperature at about 25° C. The chlorine first liberates bromine from the by-product calcium bromide and thereafter chlorine reacts with bromo dimethylhydantion.

At the end of the second halogenation step the resultant slurry of solids is filtered to remove the majority of the mother liquor, the by-product calcium chloride is thus retained in intimate mixture with the solid product. This product, which comprises 1-bromo-3-chloro-5,5-dimethylhydantoin and 1-chloro-3-bromo-5,5-dimethylhydantoin, intimately mixed with calcium chloride and water is then densified into tablet shapes or extrusions, and dried to the desired proportion of water and calcium chloride.

Solids prepared from the dihalogenated dimethylhydantoins wherein the source of the calcium chloride and water is the reaction mother liquor have exhibited the highest crush strengths. It appears that the superior crush strengths of the densified solid by either method is due to the intimately mixed nature of the finely divided solids and water.

The process of this invention may be illustrated in the following examples:

EXAMPLE I FOR COMPARISON

Bromochlorodimethylhydantoin

Water (7500 lbs.) and then dimethylhydantoin (1700 lbs.) were charged to a 2000 gallon reactor. Bromine (1061 lbs.) and sodium hydroxide (1,327 lbs. of 20% aqueous solution) were added at such a rate that 25° C. temperature was not exceeded. The pH was controlled at 6.8 to 7.0. After the bromine addition was completed, chlorine (1413 lbs.) and sodium hydroxide (3,986 lb. of 20% aqueous solution) was added at such a rate to again control the pH at 6.8 to 7.0 and the temperature at 25° C. The resultant slurry of solids containing bromochlorodimethylhydantoin was filtered, washed with water, and extruded or shaped in tablet, then dried.

EXAMPLE II

Bromochlorodimethylhydantoin—Preferred Method

In accordance with the preferred method of preparing of bromochlorodimethylhydantoin, water (7500 lbs.) and then dimethylhydantoin (1700 lbs.) were charged to a 2000 gallon reactor. Bromine (1061 lbs.) and an aqueous slurry of 246 lbs. of calcium hydroxide were added at such a rate that 25° C. temperature was not exceeded. The pH was controlled at 6.8 to 7.0. After the bromine addition was completed, chlorine (1413 lbs.) and calcium hydroxide (aqueous slurry, 738 lbs.) were added at a rate to again control the pH at 6.8 to 7.0 and temperature at 25° C. The resultant slurry of solids was filtered but not washed. By-product calcium chloride was thus retained by the solid product. The product thus produced was then densified into the desired tablet shapes and dried to the desired proportion of water and calcium chloride.

The crush strengths of bromochlorodimethylhydantoin prepared from Examples I and II were compared after densification into representative forms. The results of these tests, which are summarized in Table I below, show that halogenated hydantoins synthesized an densified in this fashion yield reproducibly higher crush strengths than those synthesized by other means.

Application of the preferred method of the present invention to the preparation of other dihalodimethylhydantoin is illustrated in Examples III and IV.

EXAMPLE III

Dibromodimethylhydantoin

Water (7500 lbs.) and then dimethylhydantoin (1700 lbs.) were charged to a 2000 gallon reactor. Bromine (2122 lbs.) and an aqueous slurry of 492 lbs. of calcium hydroxide was added at such a rate that 25° C. temperature was not exceeded, while controlling the pH at 6.8 to 7.0. Chlorine (942 lbs.) was then injected into the reaction mixture to complete the bromination, during which time an aqueous slurry of calcium hydroxide (492 lbs.) was added. The temperature was not permitted to exceed 25° C. and the pH was monitored between 6.8 and 7.0. The resultant slurry of solids containing dibromodimethylhydantoin was filtered but not washed, leaving residual by-product calcium chloride in the product. The product was then densified into the desired shapes and dried to the desired proportion of water and calcium chloride.

EXAMPLE IV

Dichlorodimethylhydantoin

Water (7500 lbs.) and then dimethylhydantoin (1700 lbs.) were charged to a 2000 gallon reactor. Chlorine (1883 lbs.) and an aqueous slurry of 984 lbs. of calcium hydroxide were added at such a rate that 25° C. temperature was not exceeded, while maintaining the pH at 6.8 to 7.0. The resultant slurry of solids containing dichlorodimethylhydantoin was filtered but not washed, leaving behind the by-product calcium chloride in the product. The product was then densified into the desired shapes and dried to the desired proportion of water and calcium chloride.

EXAMPLE V

Bromochlorodimethylhydantoin Mechanically Mixed with Calcium Chloride and/or Water for Densification The bromochlorodimethylhydantoin prepared as in Example I for Comparison was mechanically mixed with varying amounts of water and calcium chloride and the resultant particulate solids were then either extruded or compressed into tablets. Crush strenghts for such tablets containing 2.0–5.0% water and 3.0–6.0% calcium chloride by weight were measured and are reported in Table I.

From Table I it can be seen that densified halogenated dimethyl hydantoins prepared by this method and containing water or calcium chloride alone (Samples II, III) exhibit lower crush strengths than those containing mixtures of calcium chloride and water (Samples IV–VI, VIII).

From Table I it can also be seen that densified shapes of the halogenated dimethylhydantoin prepared as described in Example II were of consistently superior strength than densified shapes of the pure compound prepared as described in Example I for Comparison. When densified without additives (Sample I), the shapes had the lowest crush strengths.

When the halogenated dimethylhydantoin was mechanically mixed with water and calcium chloride the densified sample had crush strengths in the range of 60–114 pounds (Samples IV, V). Halogenated dimethylhydantoins prepared by the preferred method (Examples II–IV) and then densified exhibited the highest crush strengths in the range of 115–240 pounds (Sample V, tablets).

Extrusions of the halogenated dimethylhydantoins exhibited similar characteristics, and had crush strengths in the range of 41–51 lbs. (Sample VIII) when prepared by the preferred method (Example II), but had crush strengths of only 22–30 lbs. (Sample VII) when prepared by Example I for Comparison.

Thus, halogenated hydantoins containing calcium chloride and water are significant improvements over the conventional prior art material (Sample I), with the preferred in situ formed mixtures (Samples VI and VIII) representing the most desirable product.

TABLE I

| Sample/ Preparation Method/Additives* | Densification Product | Crush Strength |
|---|---|---|
| I. Bromochlorodimethylhydantoin prepared as described in Example I; nothing added. | Tablets- 1¼" diameter** | 8–24 lbs. |
| II. Bromochlorodimethylhydantoin prepared as described in Example V; water (.5–5%) added, mechanically mixed. | Tablets- 1¼"*** | 20–29 lbs. |
| III. Bromochlorodimethylhydantoin prepared as described in Example V; calcium chloride (1.5–10%) added, mechanically mixed. | Tablets- 1¼"*** | 0–39 lbs. |
| IV. Bromochlorodimethylhydantoin prepared as described in Example V; water (1.3%); calcium chloride (2.0%) added, mechanically mixed. | Tablets- 1¼"*** | 60–74 lbs. |
| V. Bromochlorodimethylhydantoin prepared as described in Example V; water (2.6%); calcium chloride (4.0%) added, mechanically mixed. | Tablets- 1¼"*** | 75–114 lbs. |
| VI. Bromochlorodimethylhydantoin, water (2.0–5.0%) and calcium chloride (3.0–6.0%) prepared, in situ, as described in Example II. | Tablets- 1¼"*** | 115–240 lbs. |
| VII. Bromochlorodimethylhydantoin prepared as described in Example I; nothing added. | Extrusion 5" × ¾" | 22–30 lbs. |
| VIII. Bromochlorodimethylhydantoin, water (2.0%) and calcium chloride (3.0%) prepared, in situ, as described in Example II. | Extrusion 5" × ¾" | 41–51 lbs. |

*All percent compositions are given as weight percents.
**Compressed to 75–85% of product's true density.
***Compressed to various levels of densification.

What is claimed is:

1. A method for producing densified halogenated hydantoins comprising the steps of:
   halogenating dimethylhydantoin with a first halogenation agent in the presence of water and a source of calcium and hydroxide ions in order to form a monohalogenated hydantoin intermediate;
   thereafter halogenating the monohalogenated intermediate with a second halogenation agent in the presence of water and a source of calcium and hydroxide ions, at least one of the first and second halogenation agents including a source of chlorine;
   thereafter separating dihalogenated hydantoin product from the reaction mixture without washing whereby the separated dihalogenated hydantoin product contains calcium chloride and water.

2. A method, as claimed in claim 1, and further comprising the step of forming the separated dihalogenated hydantoin product into densified shaped form.

3. A method, as claimed in claim 1, wherein the addition of the halogen and the base is monitored so as to maintain the pH of the reaction at about 6.8 to 7.0 and the temperature at about 25° C.

4. A method, as claimed in claim 1, wherein the halogenated dimethyl hydantoin product comprises about 2 to 6% calcium chloride and about 1 to 5% water by weight of the product.

5. A method, as claimed in claim 1, wherein the halogenated dimethylhydantoin is, a member selected from the group consisting of:
   dibromodimethylhydantoin;
   dichlorodimethylhydantoin;
   bromochlorodimethylhydantoin; and mixtures thereof.

6. A method for preparing halogenated dimethyl hydantoins comprising the following steps:
   introducing water and dimethylhydantoin into a reactor;

thereafter introducing a first halogen source concurrently with calcium hydroxide in a first halogenation step, the pH being maintained at about 6.8 to 7.0 and the temperature at about 25° C.;

thereafter introducing a second halogen source concurrently with calcium hydroxide in a second halogenation step, the pH being maintained at about 6.8 to 7.0 and the temperature at about 25° C.;

thereafter filtering the reaction mixture to recover halogenated hydantoin product; and compressing the recovered halogenated dimethyl hydantoin product into a shaped form.

7. In a method for producing halogenated hydantoins comprising the step of reacting dimethylhydantoin with a first halogenation agent in an aqueous reaction system while adding base to form a monohalogenated hydantoin intermediate, thereafter reacting the intermediate with a second halogenation agent while continuing to add base to form a dihalogenated hydantoin product, the improvement comprising:

using calcium hydroxide as the base; and separating the halogenated dimethylhydantoin without washing to give a product with calcium chloride and water intimately mixed therein.

8. A method, as claimed in claim 7, wherein the dihalogenated hydantoin product is bromochlorodimethyl hydantoin and wherein the first halogenation agent is bromine and the second halogenation agent is chlorine and the reactants bromine, chlorine and hydantoin are provided in substantially stoichiometric amounts of about $\frac{1}{2}$:3/2:1.

9. A method, as claimed in claim 7, wherein the halogenated dimethylhydantoin product is dibromodimethylhydantoin and wherein the first halogenation agent is bromine and the second halogenation agent is chlorine and the reactants bromine chlorine and hydantoin are provided in substantially stoichiometric amounts of about 1:1:1.

10. A method, as claimed in claim 7, wherein the dihalogenated hydantoin product is dichlorodimethylhydantoin and wherein the first halogenation agents are chlorine and the reactions therewith are carried out in a single step; and the reactants, chlorine and hydantoin are provided in substantially stoichiometric amounts of about 2:1.

11. A method, as claimed in claim 7, wherein the particulate halogenated dimethyl hydantoin is a member selected from the group consisting of:
dibromodimethylhydantoin;
dichlorodimethylhydantoin;
bromochlorodimethylhydantoin; and mixtures thereof.

* * * * *